(12) United States Patent
Gertsen

(10) Patent No.: US 7,930,941 B2
(45) Date of Patent: Apr. 26, 2011

(54) ULTRASONIC SCANNING DEVICE

(75) Inventor: Martin Gertsen, Irvington, NY (US)

(73) Assignee: Risk Management Enterprises, LLC, New York, NY (US)

( * ) Notice: Subject to any disclaimer, the term of this patent is extended or adjusted under 35 U.S.C. 154(b) by 363 days.

(21) Appl. No.: 12/117,039

(22) Filed: May 8, 2008

(65) Prior Publication Data
US 2009/0234232 A1    Sep. 17, 2009

Related U.S. Application Data

(63) Continuation-in-part of application No. 12/046,681, filed on Mar. 12, 2008.

(51) Int. Cl.
*G01N 29/265* (2006.01)
(52) U.S. Cl. .......... 73/633; 73/618; 73/620; 73/634
(58) Field of Classification Search .......... 73/634, 73/618, 620, 633; 600/459
See application file for complete search history.

(56) References Cited

U.S. PATENT DOCUMENTS

| | | | | |
|---|---|---|---|---|
| 3,369,415 A | * | 2/1968 | Slawsky | 74/89.22 |
| 4,055,988 A | * | 11/1977 | Dutton, Jr. | 73/620 |
| 4,521,764 A | * | 6/1985 | Burton | 341/138 |
| 4,841,978 A | * | 6/1989 | Eventoff et al. | 600/445 |
| 4,913,158 A | * | 4/1990 | Kikuchi et al. | 600/446 |
| 6,069,464 A | * | 5/2000 | Wu | 318/610 |

* cited by examiner

*Primary Examiner* — Jacques M Saint Surin
(74) *Attorney, Agent, or Firm* — Gottlieb, Rackman & Reisman, P.C.

(57) ABSTRACT

An ultrasonic scanner includes an assembly mounted within a housing and pivoting between two positions. The assembly includes an ultrasonic module that generates an ultrasonic beam directed at a target, such a tissue and detecting the corresponding return beam. A worm screw with a block contacting the assembly is used to selectively pivot the assembly to a desired position. The worm screw is driven by a DC motor and the position of the assembly is monitored using a proximity sensor, such as a Hall Effect Device. A hybrid controller in one mode receives analog signals from the Hall Effect Device and uses them as a feedback signal to an analog OP AMP driving the DC motor to move said assembly to a predetermined position. In another embodiment, the motor is activated for a predetermined time to move the assembly by a predetermined amount.

19 Claims, 5 Drawing Sheets

ULTRASONIC SCANNING DEVICE

RELATED APPLICATIONS

This application is a continuation-in-part of application Ser. No. 12/046,681 filed Mar. 12, 2008 and incorporated herein by reference.

BACKGROUND OF THE INVENTION

A. Field of Invention

This invention pertains to an ultrasonic scanner incorporating a linear scanning device, and more particularly, a scanning device with a hybrid analog-digital controller incorporating a Hall effect device as a feedback or position sensor and a DC motor.

B. Description of the Prior Art

Many electronic instruments include an element or component that is moved or positioned very accurately in order to insure that a desired parameter is measured properly, that a mechanical or electromagnetic force is applied at a desired location or that a physical phenomenon is measured properly. For example, ultrasonic scanner devices typically include an ultrasonic transducer that directs an ultrasonic beam at biological tissues or other samples of interest and a detector that detects the ultrasonic beam reflected from various layers within the tissues or samples. The resulting signals are then analyzed and information is produced about various aspects of the tissues, or sample, such as, for example, their internal structure. Normally, information is sought for not just a single point within the tissues but with regard to a whole area or zone. In order to obtain this information, it is necessary to move the transducer and the detector by a predetermined distance. Often in such a situation, a scanning operation is performed wherein a signal is obtained when the transducer and the detector are at a predetermined location, the transducer and detector are moved by a small amount and a new signal is obtained. This process can be repeated numerous times until the whole area or zone of interest within the tissue or sample has been scanned.

There are many prior art scanners that obtain information about tissue structures and other similar information by using the scanning operation described above. The scanning operation could be accomplished using either analog or digital techniques. Purely analog techniques may not be ideal for this type of operation because they may not be accurate enough, especially if the incremental movement required is very small. That is why existing devices (such as the transducers available from Capistrano Labs, Inc., San Clemente, Calif. 92672) use a digital scheme requiring stepping motors, digital resolvers and other expensive and complicated precision components.

The present inventor has discovered that this problem is solved by using a hybrid analog/digital control scheme, as described below.

SUMMARY OF THE INVENTION

Briefly, an ultrasonic scanner constructed in accordance with this invention includes an elongated assembly having one end pivotably mounted by a hinge in a housing and supporting an ultrasonic module at a second end. The ultrasonic module generates a beam of ultrasonic sound pulses in a direction parallel with the longitudinal axis of the assembly, and the echoing sounds are detected and used to generate information about a tissue or other sample or target of interest. More particularly, the echoing sounds detected by the module are used to generate a two-dimensional image of the target. In a preferred embodiment, in the subject apparatus, the ultrasonic transducer module is placed at several predetermined points that are equidistant from each other and are disposed generally along a trajectory normal to the axis of the module. At each point a two-dimensional image is obtained as described above. In this manner a plurality of two-dimensional images are collected, which can then be combined to generate a three-dimensional image.

A mechanism with a hybrid controller is used to pivot the assembly. The mechanism includes a worm screw disposed in the housing. One end of the worm screw is engaged by a small DC motor so that the worm screw can be selectively turned in one direction or another around its longitudinal axis. The other end of the worm screw passes through a threaded hole in a block. The block is restrained within the housing so that it can be translated or reciprocated along the axis of the worm screw as the screw is turned in one direction or another. The axes of the assembly and the worm screw are disposed at an angle and a side surface of the block is in contact with a side surface of the assembly. As a result, as the worm screw turns and translates the block, the block causes the assembly to move in a camming action.

The position of the assembly is monitored using a position sensor that may be a proximity sensor, preferably incorporating a Hall effect device and a magnet. This device generates a signal that is indicative but not normally linearly proportional to a distance between two elements of the assembly.

A hybrid controller is used to operate the motor. The controller includes an analog operational amplifier and a translator that receives the signal from the position detector and translates into a corresponding signal indicative of actual distance. The controller receives a command to pivot the assembly to a certain position. This command and the output of the translator are fed to the operational amplifier which then activates the motor and pivots the assembly until the desired position is reached using the signal from the sensor for feedback.

In an alternate embodiment, the feedback signal is used for large movements of the assembly, such as to some end points or center point. For incremental movement between frame scans, a pulse is used to activate a low friction, high torque electric motor/reduction-gear/worm screw combination which then pivots the assembly very accurately,

DETAILED DESCRIPTION OF THE INVENTION

Figure 1:
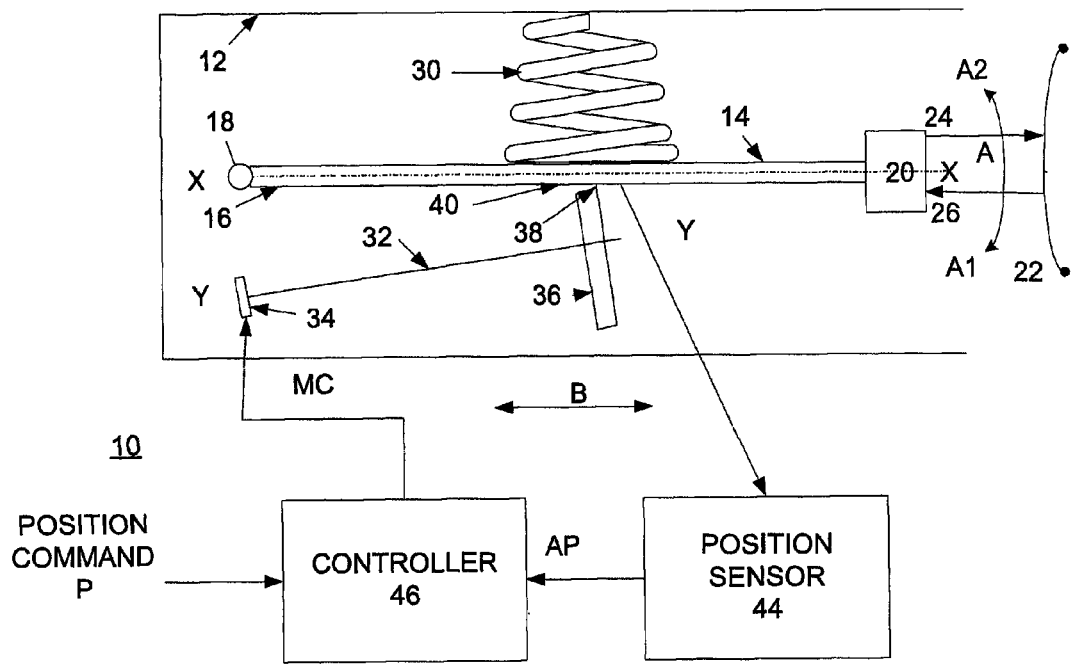
FIG. 1 shows a somewhat diagrammatic view of an ultrasonic scanner constructed in accordance with this invention.

In FIG. 1, for the sake of clarity, a very diagrammatic side view of an ultrasonic scanner constructed in accordance with this invention is presented. The scanner 10 includes a housing 12 with a rod-shaped ultrasonic assembly 14. The assembly 14 is pivotably attached at one end 16 to the housing 12 by a hinge 18. At the opposite end, the assembly 14 has a head 20. The hinge 18 allows the head to move or pivot along an arc A extending between points A1 and A2 as it is disposed near a target such as tissue 22 or other sample of interest. The head 20 includes an ultrasonic module including an ultrasonic source (not shown) that generates short ultrasonic pulses 24 toward the tissue 22. The module further includes a detector (not shown) that detects the echoing pulses 26 returned from the tissue 22. The signals from the detector are then analyzed using known methods, which do not pertain to the present invention, and, accordingly, shall not be described.

A biasing spring 30 is disposed between a sidewall of the housing 12 and the assembly 14. This spring biases the assembly 14 so that its longitudinal axis X-X passes through point A1. The purpose of the present invention is to selectively deflect the assembly from this first position toward any intermediate point desired. The furthest that the assembly 14 can travel is the angle at which its axis X-X passes through point A2. For this purpose, the scanner 10 is provided with a worm screw or lead screw 32 having a longitudinal axis Y-Y. (For the purpose of clarity, in FIG. 1, only the axis of the worm screw is shown). The ends of the worm screw 32 are supported so that the axis Y-Y within the housing 12 remains fixed. A motor 34 engages one end of the worm screw 32. The motor 34 is provided to rotate the worm screw 32 selectively clockwise or counterclockwise about axis Y-Y.

A block 36 with a threaded hole (not shown) is mounted on the worm screw 32 and is captured by guides (not shown) that limit the block 36 to a translational or reciprocating movement, as indicated by arrow B. That is, when the worm screw 32 is turned in one way, the block 36 moves to the right along arrow B, when the worm screw is turned the other way, the block 36 moves linearly in the opposite direction. In this manner, the rotational movement of the worm screw 32 is transformed into a translational or reciprocating movement of block 36.

The block 36 has a lateral contact surface 38 facing and contacting a side surface 40 of the assembly 14. The spring 30 pushes the assembly 14 and it's contact surface 40 against the contact surface 38. Because the two axes X-X and Y-Y are disposed at an angle, the block 36 and the spring 30 cooperate to cause the assembly 14 to pivot in one direction or another, depending on whether the block 36 moves to the left or the right. Thus the block 36, worm screw 32 and motor 34 together form a pivoting mechanism for pivoting the assembly 14 around hinge 18 by generating a camming force between the contact surfaces 38 and 40.

The position of the assembly 14 can be determined in many different ways. For example, the angular position of the worm screw 32 is directly related to this position and therefore it may be determined by counting the number of revolutions of the screw. However, the assembly position can be determined more accurately using an active sensor. For example, the device 10 can include a position sensor 44 which determines the position of the assembly 14 with respect to a predetermined reference point and generates an appropriate position signal, as described in more detail below.

The device 10 generally operates as follows. A controller 46 receives a position command P from an external source (such as a command signal generator 90 shown in FIG. 7 and discussed in more detail below). The controller 46 also receives a position signal AP from the position sensor 44 and it compares this signal to the position command P. The controller then sends an appropriate control signal MC to motor 34. The motor 34 turns the worm screw 32 either clockwise or counterclockwise depending on whether the assembly 14 has to pivot towards point A1 or A2. The rotation of the worm screw causes the block 36 to move in the appropriate direction thereby causing the assembly 14 to pivot. The position of the assembly 14 is detected and indicated by the position sensor 44. When the desired position, i.e., the position requested by the position command is reached, the controller cuts off the control signal to the motor 34 and the motor 34, block 36 and assembly 14 stop moving.

Figure 2:
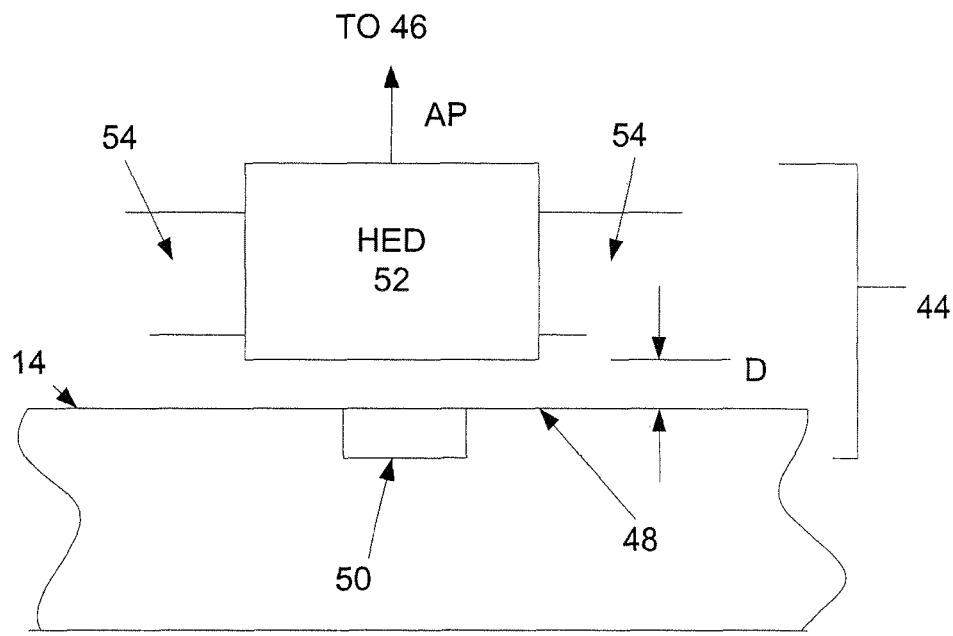
FIG. 2 shows a proximity sensor used for the scanner in FIG. 1.
Figure 3:
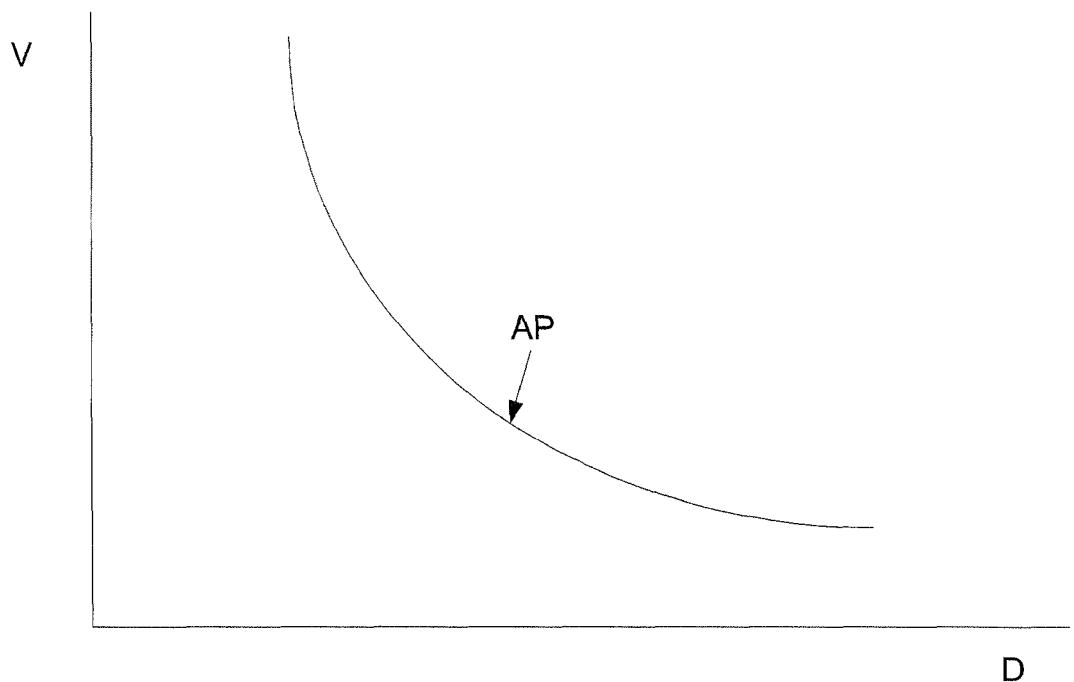
FIG. 3 shows the response of the sensor of FIG. 2.

The position sensor 44 can be implemented in a number of different ways. The present inventor has found that a Hall Effect Device (HED) is particularly useful for this purpose. A sensor using such a device is illustrated in FIG. 2. In this figure, a surface 48 of assembly 14 is provided with a magnet 50. The magnet can be attached to the surface 48 or it can be imbedded in it. An HED 52 is disposed adjacent to the magnet 50 and is affixed to the housing 12 by a pair of brackets 54 or other similar means. The HED 52 sends an analog position signal AP to the controller 46. As is well known in the field, the signal AP generated by the HED 52 is generally a function of the distance D between the HED 52 and magnet 50. In fact, a typical HED 52 generates a voltage output (that is, signal AP) that is a hyperbolic function of the distance D as shown in FIG. 3. Other proximity sensors may also be used, instead of one using an HED. Moreover, the sensor can be used to measure the distance D directly, as shown in FIG. 2, or indirectly, for example by measuring the position or movement of the block 36.

Figure 4:
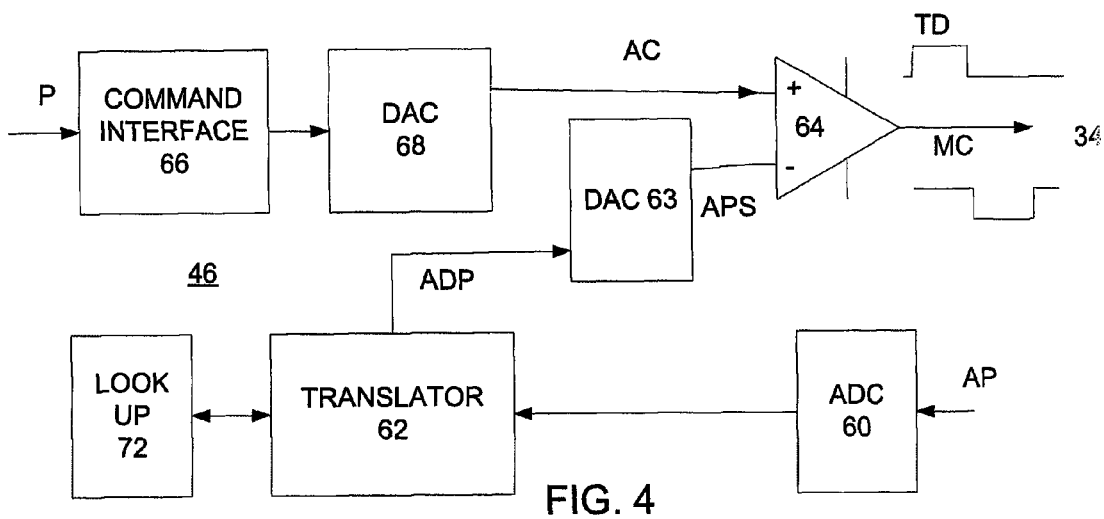
FIG. 4 shows a block diagram of the hybrid control scheme used in the scanner of FIG. 1.

FIG. 4 shows a block diagram of the controller 46. The controller 46 includes an A/D converter 60 that receives the signal AP and converts it to a corresponding digital signal. The digital signal is then provided to a translator 62. The purpose of the translator 62 is to provide an adjusted position signal ADP. This adjusted position signal is generated using a translation function corresponding to the curve of FIG. 3. In other words, the signal ADP is a digital signal that indicates the actual position of the assembly 14 based on the signal AP from the HED 52. This signal ADP is converted to an analog position signal APS by D/A converter 63 and fed to the inverting input of an operational amplifier (OPAMP) 64. OPAMP 64 is a standard analog amplifier that is provided with various standard biasing and filtering circuits designed to insure that the OPAMP 64 has a limited gain at low frequencies. A method of determining the function used by the translator 62 is described below.

The controller 46 also includes a command interface 66 receiving a position command P. This command P is preferably received from a PC, a user interface, or any other source and is usually a digital signal and is converted into an analog command AC, and this command AC is then fed to the non-inverting input of OPAMP 64. The OPAMP 64 compares the two signals AC and APS and generates a motor control signal MC that is either a positive pulse if this difference indicates that the motor 34 has to turn in one direction or a negative pulse if the motor has to turn in the other direction. The rotation of the motor causes the assembly 14 to pivot to the position requested by the position command P. The HED 52 tracks the position of the assembly 14. When the requested position is reached, the difference between signals AC and APS is zero and the output of OPAMP 64 drops to zero as well. Thus, the duration TD of the pulse is equal to the time that it takes for the assembly 14 to pivot from an initial position to the requested position.

The translator 62 is preferably an ASIC chip or other similarly custom made element. It can be set to perform in several different ways. The easiest, but perhaps not the most reliable way is to use the published specs that are provided by the manufacturer of the HED 42. A more reliable way is to have the motor 34, block 36 and assembly 14 cooperate to pivot one or more times between points A1, A2 with stops at several intermediate points therebetween. At each intermediate point, the distance D and the corresponding voltage AP output by the HED are measured and recorded. A curve fitting program is then used to determine the function correlating the voltage AP to the distance D. As indicated above, this function is normally a hyperbolic curve. The function is then programmed into the translator 62, and each time the translator 62 receives a signal AP, it is translated into corresponding signal ADP.

Yet another approach is to repeat the process described above, but instead of generating a function, a look-up table 72 can be created. In this implementation, for each value AP, the translator 62 looks up the corresponding signal ADP in a look-up table 72.

Of course, strictly speaking, the distance D detected by device 52 is not the important parameter. The important parameter is the distance that head 20 moves as a result of the rotation of the worm screw 32. However, this latter distance is proportional to distance D and therefore, the translator 62 automatically scales distance D accordingly. For example, if the device 52 is disposed at the middle of the assembly 16, the distance D is automatically doubled.

As mentioned above, the device 10 is an ultrasonic scanner, and as such can be used in several different ways. One way is to point it at a particular direction using the position command and then obtain a two-dimensional picture of the target with head 20. However, a more common practice is to scan the tissue or other target and generate a plurality of two-dimensional images that can be converted into a corresponding 3-D image. For this purpose, commands can be generated, for example, from a PC to, move the assembly 14 so that it is pointing at A1. Then assembly 14 can be sequentially pivoted to many intermediate positions between A1 and A2 and ultrasonic signals can be collected at each. For this operation, the controller 46 can be connected to a standard PC, which then generates the positioning commands sequentially. A standard connection can be used for this purpose, such as a USB connector. For a typical 3-D ultrasonic image the head 12 is moved 5 mm in increments of 10μ. The device 10 performs this operation very fast and accurately.

Figure 5:
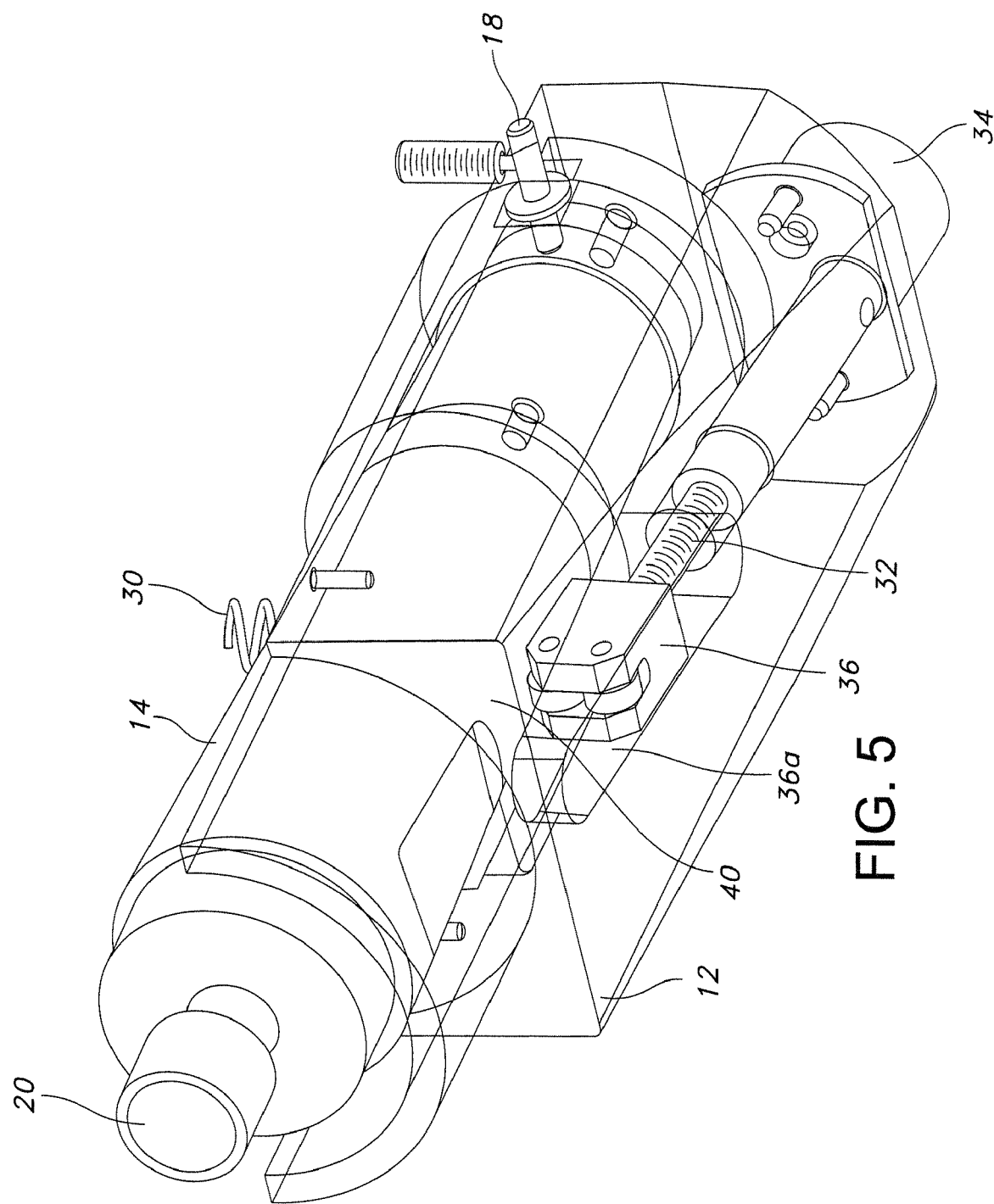
FIG. 5 shows a first isometric view of the ultrasonic scanner of FIG. 1 with portions cut out to show the inner elements thereof.
Figure 6:
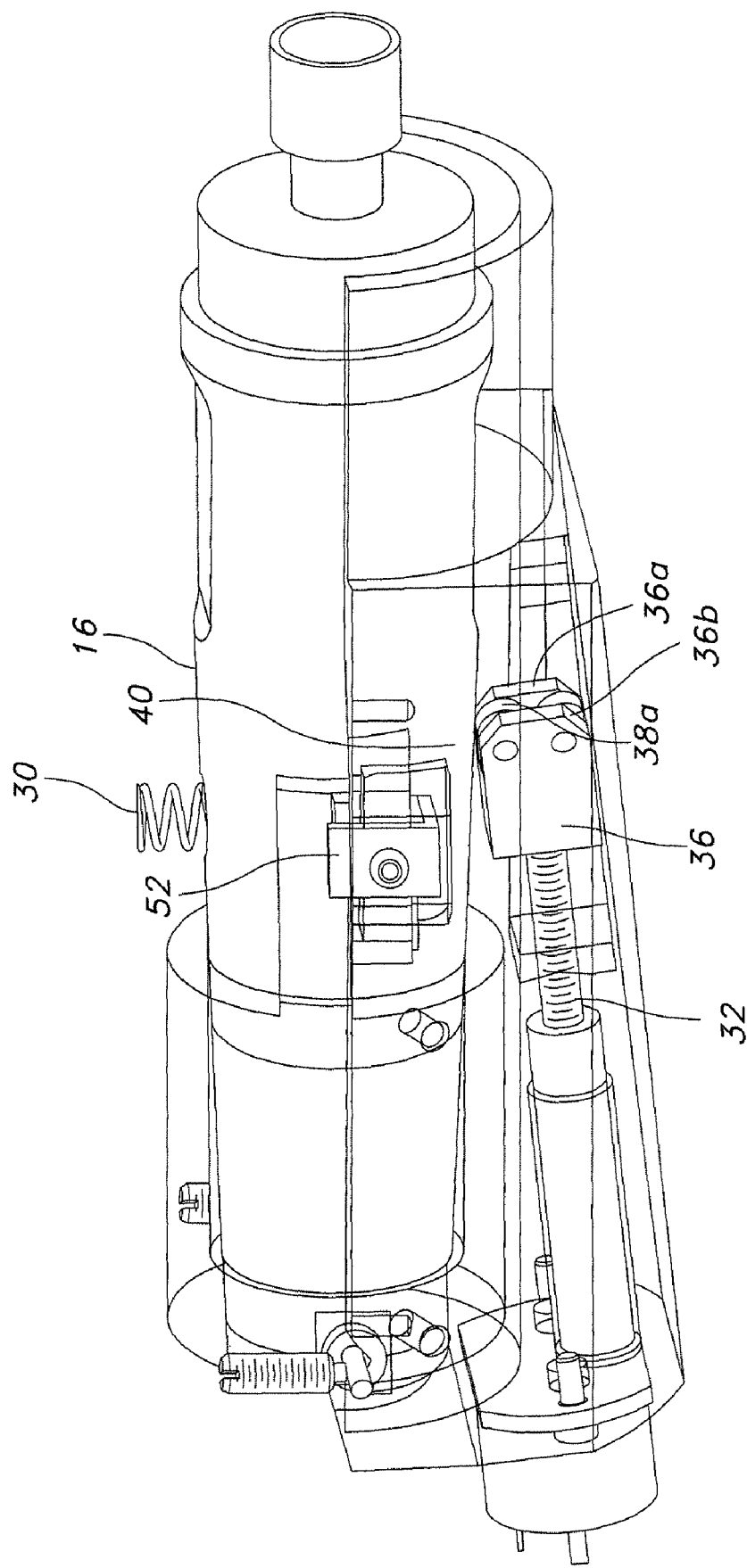
FIG. 6 shows a second isometric view of the ultrasonic scanner of FIG. 1.

In FIGS. 1 and 2, the device 10 is illustrated somewhat diagrammatically, with many elements being omitted, and other elements being shown with disproportionate dimensions. In FIGS. 5 and 6 the device 10 is represented more realistically. As illustrated in these figures, the block 36 is accommodated in a guide 36A, which limits its movement to a linear motion. In other words, guide 36A insures that the block 36 does not rotate with worm screw 32.

In addition, as is clear from these drawings, preferably, the block 36 is provided with two rollers 38A and 36B. Roller 38A provides the contact with surface 40 of the assembly 16. In this manner, frictional forces between the block 36 and assembly 16 are reduced considerably to insure that the motion of block 36 is transmitted smoothly to the assembly 16 and to reduce wear and tear on these elements. Similarly roller 36B eliminates or reduces friction between the block 36 and its guide 36A.

Basically, in a typical scanning procedure, the apparatus operates in one of two modes. In a first mode, the head 20 is situated either in a center position, or at one of the end points A1, A2 and must be pivoted to another specific position. In a second mode, the head 20 starts from a specific position, typically point A1 and is pivoted in minute increments through many intermediate positions towards a second specific position, typically A2. At each intermediate position, a scan is performed and data is collected as described above.

In the first embodiment of the invention, the assembly 14 is moved or pivoted in either mode by using the controller 40 shown in FIG. 4. In another embodiment of the invention shown in FIG. 7, controller 40A is modified so it operates in one of two modes. In this embodiment, a command signal generator 90 is used to generate commands for the controller. The command signal generator may be a PC or part of a device that controls the whole scanning operation.

Figure 7:
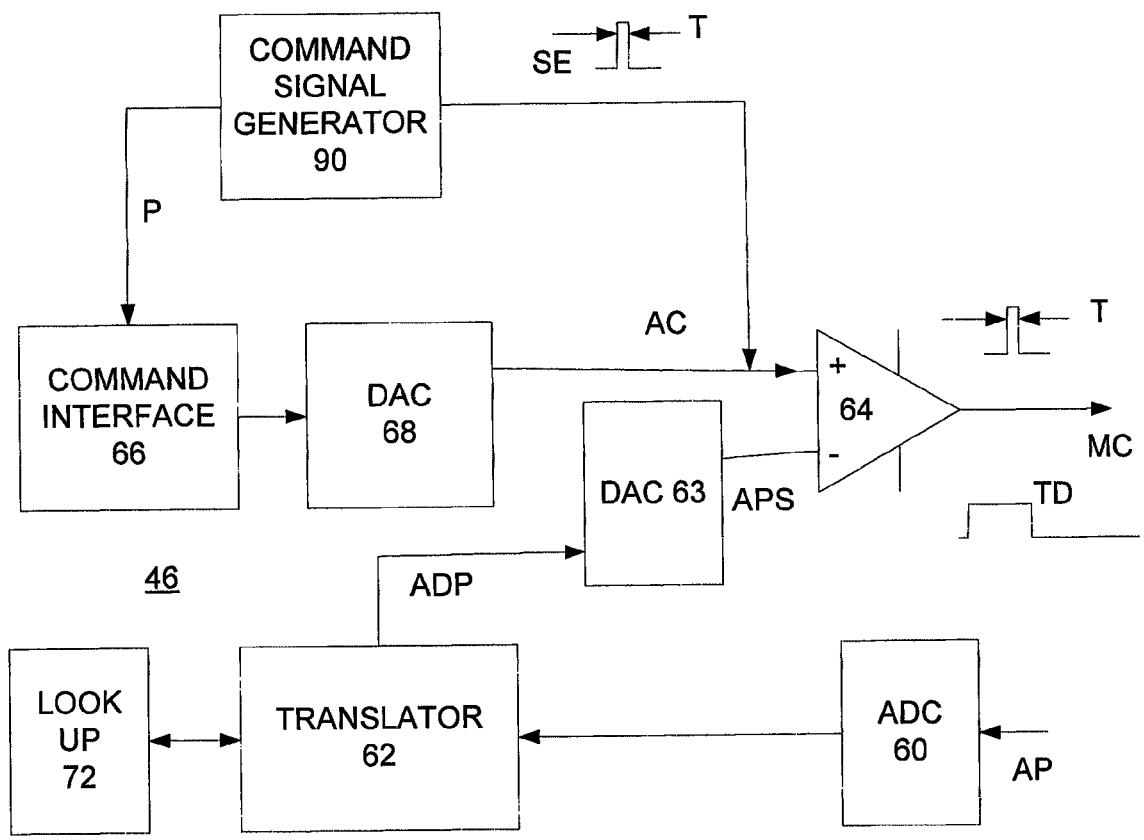
FIG. 7 shows an alternate embodiment of the invention.

As seen in FIG. 7, the generator 90 generates one of two signals: P or SE. Signal P, as described above, designated the desired position of the assembly 14. When this signal is received, the modified controller 40A operates as described above, in conjunction with FIG. 4. Signal SE is preferably in the shape of a pulse having an amplitude that saturates the amplifier 64 and a duration T. This duration T is selected to activate the motor 34 for a period sufficient to move the assembly 14 by a predetermined incremental distance d. The head 20 on assembly 14 is activated to perform a scan. When the scan is completed, the command signal generator 90 generates a new signal SE. In other words, a signal SE is generated for every scanning frame.

Amplifier 64 includes a standard biasing circuitry (not shown in detail) that controls its gain, its slew rate and other characteristics. For the present invention, the amplifier is overdamped and its other characteristics are selected so that its slew rate in response to the signal SE is very high. As a result, the output of the amplifier follows the signal SE very closely, allowing the signals to have a very short duration T in the order of microseconds.

Because the motor 34 is enclosed in housing 12, it is necessary to keep its size as small as possible. However, inherently, a small motor could not generate sufficient torque to turn worm screw 32 without a gear box. Therefore, in the present invention, the motor 34 includes a standard gear box, provided integrally within the motor housing and that couples the motor shaft (not shown) to the worm screw 32. Preferably, the motor 34 with its gear box is capable of generating a high torque with low friction. For example, the motor 34 at nominal voltage can be operating at around 12,800 rpm and have a 6:1 reduction gear box. Worm screw 32 can have a pitch of 40 threads/in. In this combination, the motor 34 can rotate the worm screw 32 very effectively.

The described motor/gear-box/worm screw combination has a further advantage. It is well known that once a body is set in motion, its inertia prevents it from coming to rest instantaneously and, instead it requires a finite time and distance to come to rest. Moreover, because of friction and other non-linear effects, the exact time and rest position are indeterminate. Therefore in many systems requiring highly accurate and reproducible results, special and expensive measures must be taken for inertial effects. However, the inventor has found that the structure described above has very little inertial effects. As a result, the assembly 14 can be pivoted very accurately in small increments (e.g., in the range of 5 μm) without any additional elements or even the need for a feedback loop. Therefore the apparatus described herein can be implemented easily using inexpensive parts.

The controller 40A in FIG. 7 operates in the second mode as follows. The amplifier 64 receives signal SE having a duration or pulse width T, It immediately saturates and generates an essentially identical output motor control signal MC. This motor control signal MC turns on the motor 34 causing the worm screw 32 to rotate and move the assembly 14. At the end of period T, the output of amplifier 64 drops to zero, and motor 34 and worm screw 32. The period T is determined from the electrical characteristics of the motor 34, its physical characteristics, and the dimensions of the worm screw 32 and the assembly 14. As discussed above, T is selected to move the assembly 14 in predetermined increments of, e.g., 5 μm. In this mode of operation, the feed back signal APS never catches up to the signal SE and in essence, it is ignored.

As discussed above, in the modified controller 40, the operational amplifier 64 is used to generate the motor control signal MC in both modes of operation. Alternatively, a separate amplifier may be used for each mode.

Numerous modifications may be made to this invention without departing from its scope as defined in the appended claims.

I claim:

1. An ultrasonic scanner comprising:
   an assembly having a transducer module selectively generating ultrasound pulse directed at a target and detecting the corresponding echoing pulses, said assembly having a contact surface;
   a pivoting mechanism including a worm screw, a motor selectively rotating the worm screw about its longitudinal axis and a block engaged by the worm screw and being moved linearly by said worm screw, said block being positioned adjacent to said contact surface to cause said assembly to pivot when said worm screw turns; and
   a controller selectively rotating said worm screw for positioning said assembly, wherein said controller operates in a first mode in which a feedback signal is used indicative of the actual position of said assembly and a second mode in which the motor is operated for a predetermined time period independently of said feedback signal.

2. The ultrasonic transducer of claim 1 wherein said assembly is attached by a pivoting point to a stationary member and is pivoted in a plane about said pivoting mechanism.

3. The ultrasonic transducer of claim 1 further comprising a spring biasing said assembly toward a first position, said assembly being pivoted away from said first position by said block.

4. The ultrasonic transducer of claim 1 wherein said controller is a hybrid controller receiving a digital command to position said assembly and generating a corresponding command to said motor.

5. The ultrasonic transducer of claim 4 further comprising a detector that detects a current position of said assembly.

6. The ultrasonic transducer of claim 5 wherein said controller includes a feedback control circuit receiving a signal from said detector as a reference signal.

7. An ultrasonic scanner comprising:
   a housing;
   an assembly having an elongated body pivotably attached to the housing at one end, and having an ultrasonic module at the other end and a contact surface there between said ultrasonic module selectively generating signals characterizing a target;
   a pivoting mechanism including a worm screw disposed in the housing, a motor selectively rotating said worm screw and a block mounted on the worm screw, said block being driven linearly when the worm screw is rotated, said block engaging said contact surface to cause said assembly to pivot about said one end; and
   a controller including a position sensor for sensing the position of the assembly; said controller being adapted to selectively operate in a first mode in which said assembly is moved from a first to a second position by generating a first output signal to said motor that is based on a current position of said assembly as determined by said sensor; said controller operating in a second mode in which said controller generates a second signal to move said assembly by a predetermined amount independently of said position sensor.

8. The ultrasonic scanner of claim 7 wherein said sensor includes a magnet disposed on said assembly and a Hall Effect Device (HED) disposed on said housing and arranged to measure a distance to said assembly.

9. The ultrasonic scanner of claim 8 wherein said controller includes an operational amplifier having a first input receiving a position command and a second input receiving a feedback signal related to said distance and an output used for driving said motor in said first mode, said operational amplifier receiving a pulse having a duration related to said predetermined amount in said second mode.

10. The ultrasonic scanner of claim 9 wherein said controller receives a digital position signal and further includes a first D/A converter to convert said digital position signal into an analog command.

11. The ultrasonic scanner of claim 10 further comprising a second A/D converter receiving an analog signal from said sensor and generating a corresponding digital sensor signal corresponding to said sensor signal.

12. The ultrasonic scanner of claim 11 further comprising a translator that translates said digital sensor signal into a distance signal, said distance signal being used as said feedback signal.

13. The ultrasonic scanner of claim 12 wherein said translator uses a preset formula to generate said distance signal, said preset formula being related to a physical characteristics of said HED.

14. The ultrasonic scanner of claim 12 wherein said translator includes a look-up table for converting said digital sensor signal into said distance signal.

15. A device comprising:
   a housing;
   an assembly having a first end pivotably mounted in said housing and a second end disposed opposite said first end;
   a pivoting mechanism disposed in said housing for pivoting said assembly with respect to said first end, said pivoting mechanism including an electric motor, a worm screw extending at least partially along said assembly and being selectively rotated about its longitudinal axis by said motor, and a block mounted on said worm screw and arranged to apply a caming force on said assembly to cause it to pivot with respect to said first end; and
   a controller selectively rotating said worm screw for positioning said assembly, wherein said controller operates in a first mode in which a feedback signal is used indicative of the actual position of said assembly and a second mode in which the motor is operated for a predetermined time period independently of said feedback signal.

16. The device of claim 15 wherein said motor is coupled to said worm screw by a reduction gear.

17. The device of claim 15 further comprising a sensor sensing a current position signal of said assembly and generating a corresponding position signal.

18. The device of claim 17 wherein said controller operates in an alternate mode in which it receives said current position signal to move said assembly to a predetermined position.

19. The device of claim 17 wherein said sensor is a Hall Effect device.

* * * * *